(12) United States Patent
Choi

(10) Patent No.: US 6,297,397 B1
(45) Date of Patent: Oct. 2, 2001

(54) METHOD FOR PRODUCING HIGHLY PURE TETRASODIUM SALT OF ETHYLENEDIAMINETETRAACETIC ACID

(75) Inventor: Cheong-Song Choi, Seoul (KR)

(73) Assignee: Tong Suh Petrochemical Corp., Ltd., Ulsan (KR)

(*) Notice: Subject to any disclaimer, the term of this patent is extended or adjusted under 35 U.S.C. 154(b) by 0 days.

(21) Appl. No.: 09/555,584

(22) PCT Filed: Sep. 24, 1998

(86) PCT No.: PCT/KR98/00294

§ 371 Date: Jun. 1, 2000

§ 102(e) Date: Jun. 1, 2000

(87) PCT Pub. No.: WO99/29656

PCT Pub. Date: Jun. 17, 1999

(30) Foreign Application Priority Data

Dec. 9, 1997 (KR) .................................................. 97/67060

(51) Int. Cl.⁷ .................................................. C04C 229/00
(52) U.S. Cl. ............................................. 562/566; 562/565
(58) Field of Search .................................. 562/566, 565, 562/554

(56) References Cited

U.S. PATENT DOCUMENTS 2,407,645 * 9/1946 Bersworth et al. .
2,845,457 * 7/1958 Kroll et al. .
2,860,164 * 11/1958 Kroll et al. .

OTHER PUBLICATIONS

Derwent Abstract (1981–06727D) of JP 55151537 A. Nanbu et al. Crystallising sodium EDTA salt—by concentrating under reduced pressure to ppte. pure crystals. Nov. 1980.*

Derwent Abstract (1982–34298E) of JP 57048949 A. Wada et al. Ethylene diamine tetraacetic acid alkali metal salt prepn.—by adding caustic alkali to aq. soln to EDTA alkali metal and sepg. out crystals pptd. Mar. 1982.*

Ault, Addison. Techniques and Experiments for Organic Chemistry, 1987. pp 55–56.*

* cited by examiner

Primary Examiner—Paul J. Killos
Assistant Examiner—Mahreen Chaudhry
(74) Attorney, Agent, or Firm—Harrison & Egbert

(57) ABSTRACT

A method for producing highly purified crystals of tetrasodium. Salt of ethylenediaminetetraacetic acid including reacting ethylene diamine, NaCN and formalin in the presence of an alkali to yield a solution containing EDTA4Na and impurities. This solution is subjected to crystallization over a solvent to form EDTA4Na crystals. The solvent is a mixture of methanol and an alcohol of either ethanol or propanol. The methanol has a ratio by weight to the alcohol of 1:0.43–4.0. The EDTA4Na crystals are then recovered after subjecting the solution to crystallization.

3 Claims, 3 Drawing Sheets

METHOD FOR PRODUCING HIGHLY PURE TETRASODIUM SALT OF ETHYLENEDIAMINETETRAACETIC ACID

BACKGROUND OF THE INVENTION

1. Field of the Invention

The present invention relates to a method for producing high purity tetrasodium salt of ethylenediaminetetraacetic acid(EDTA-4Na). More particularly, it relates to a method for producing high purity and uniform crystals of EDTA-4Na from an aqueous solution of crude EDTA-4Na by crystallization using a mixed solvent.

2. Description of the Related Art

Tetrasodium salt of ethylenediaminetetraacetic acid ('Tetrasodium EDTA' or EDTA-4Na) is a white crystalline powder of no taste and no odor. It has a good solubility in water (103 g/100 ml water), although it is rarely soluble in organic solvents such as alcohols or ethers, etc.

EDTA-4Na and its derivatives, which act as sequestering agents or chelating agents, have a wide range of applications in dyeing, photographs, cosmetics, cleaning agents and synthetic resin industries, and the like. They are employed to avoid problems associated with metal ions in water or aqueous solutions by forming chelate complexes of the metal ions.

It may be prepared by reacting ethylene diamine, NaCN and formalin in the presence of an alkali at 60–150° C. as shown in Reaction Scheme 1 below to yield an aqueous solution of crude EDTA-4Na. When by-product ammonia is removed under reduced pressure, a solution of crude EDTA-4Na of about 40–50% purity is obtained. The solution still contains a large amount of impurities such as unreacted reactants and by-products (JP 57-45425A, JP 56-3930 A, U.S. Pat. No. 2,860,164).

Reaction Scheme 1

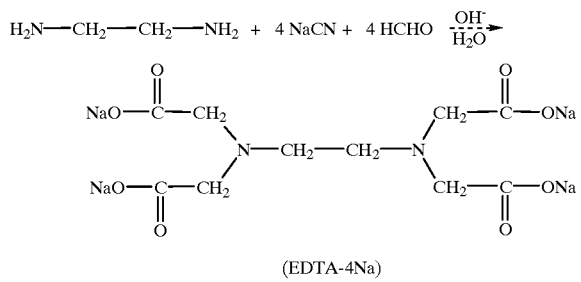

These impurities limit the applications of the product EDTA-4Na and it is required to recover purified EDTA-4Na by various purification method in order to use it in foodstuffs or cosmetic industries, etc.

Crystallization based on solubility difference over temperature range is not efficient for purifying EDTA-4Na because the difference is not significant as shown in FIG. 1.

Four typical methods for recovering crystals of EDTA-4Na have been known.

In one method so called 'total drying', the aqueous solution of crude EDTA-4Na of about 40% purity is dried by using spray dryer. This method yields only low purity EDTA-4Na product and cannot obtain high purity product.

In a second method, the aqueous solution of crude EDTA-4Na (about 40% purity) was adjusted to lower than pH 2 with HCl to precipitate an insoluble acid form of EDTA (U.S. Pat. No. 2,860,164). The acid form of EDTA obtained is washed with a large amount of water to completely remove by-product salts and four(4) equivalents of NaOH is added thereto to yield high purity EDTA-4Na (Reaction Scheme 2).

Reaction Scheme 2

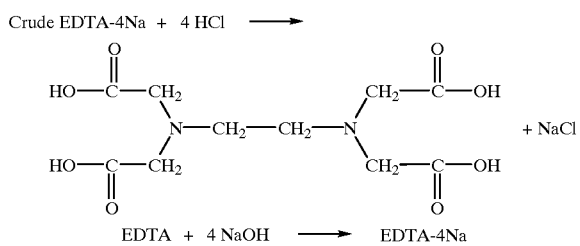

Although this method produces high purity EDTA-4Na, it still has several problems in association with the steps of crude EDTA-4Na→EDTA→EDTA-4Na. Thus, the reaction of crude EDTA-4Na and HCl gives a reaction waste containing a large amount of by-product salts and the addition of NaOH to Na-free EDTA to obtain EDTA-4Na increases production cost.

In a third method, 50% NaOH is used to salt out EDTA-4Na crystals (JP 62-61022B). This method produces an excessive NaOH-containing waste which causes environmental pollution, making it commercially disadvantageous.

In a fourth method, a single organic solvent, in particular methanol is used to precipitate high purity EDTA-4Na crystals. This method still has several problems in that the yield is not satisfactory and that the crystals of EDTA-4Na obtained are distributed in a wide range of particle diameters and the microparticles having a diameter less than about 30 μm occupy a large portion, requiring a long filtration time for recovery, that eventually contributes to the decrease in productivity (Comparative Examples 2–9).

Therefore, a new effective method for recovering high purity EDTA-4Na is needed.

BRIEF SUMMARY OF THE INVENTION

An object of the present invention is to provide a method for producing highly purified EDTA-4Na with a higher yield in an economic manner.

Another object of the present invention is to provide a method for recovering highly purified uniform crystals of EDTA-4Na from a solution containing EDTA-4Na and impurities, wherein said solution is subjected to a crystallization using a mixed solvent of methanol and an alcohol other than methanol.

The present invention provides a method for producing highly purified crystals of tetrasodium salt of ethylenediaminetetraacetic acid (EDTA-4Na), which comprises the steps of reacting ethylene diamine, NaCN and formalin in the presence of an alkali to yield a solution containing EDTA-4Na and impurities;

subjecting the solution to crystallization over a solvent to give EDTA-4Na crystals; and recovering the EDTA-4Na crystals, wherein said crystallization solvent is a mixture of methanol and an alcohol other than methanol.

The above and other objects, features and applications of the present invention will be apparent to those of ordinary skill by the following detailed description.

DETAILED DESCRIPTION OF THE INVENTION

The present invention provides a new and effective method for recovering highly purified crystals of EDTA-4Na from a solution containing EDTA-4Na and impurities, which yields uniformly sized crystals and eliminates cost problems associated with the conventional methods. Further, it renders a recycling of the crystallization alcohol solvents.

EDTA-4Na is usually prepared by reacting ethylene diamine, NaCN and formalin in the presence of an alkali at 60–150° C. to yield an aqueous solution containing about 40–50 wt % of crude EDTA-4Na. Ammonia, a by-product is then removed and the reaction product is purified by various known methods.

According to the present invention, a solution containing EDTA-4Na and impurities, which is prepared by reacting ethylene diamine, NaCN and formalin, is subjected to crystallization using a mixed solvent of methanol and an alcohol other than methanol. The solution usually contains about 40–50 wt % of EDTA-4Na.

The alcohols other than methanol employed for the present invention may include smaller alcohols, and in particular those having 2–4 carbon atoms such as ethanol, propanol, butanol or their isomers. The mixing ratio of methanol to other alcohols is in the range of 0.1–10.0: 1 by weight. The ratio of the mixed solvent to crude EDTA-4Na (purity of 40 wt %) is in the range of 0.8–5.0: 1 by weight.

The crystallization may be performed at 40–70° C., and preferably 50–70° C. The resulting crystals have a narrow distribution of particle size, for example they contain less than 11 wt %, and preferably less than 10 wt % of particles having a diameter less than 30 μm.

EXAMPLES

The present invention will be described in more detail by way of various Examples, which should not be construed to limit the scope of the present invention.

Reference Example 1

Figure 1:
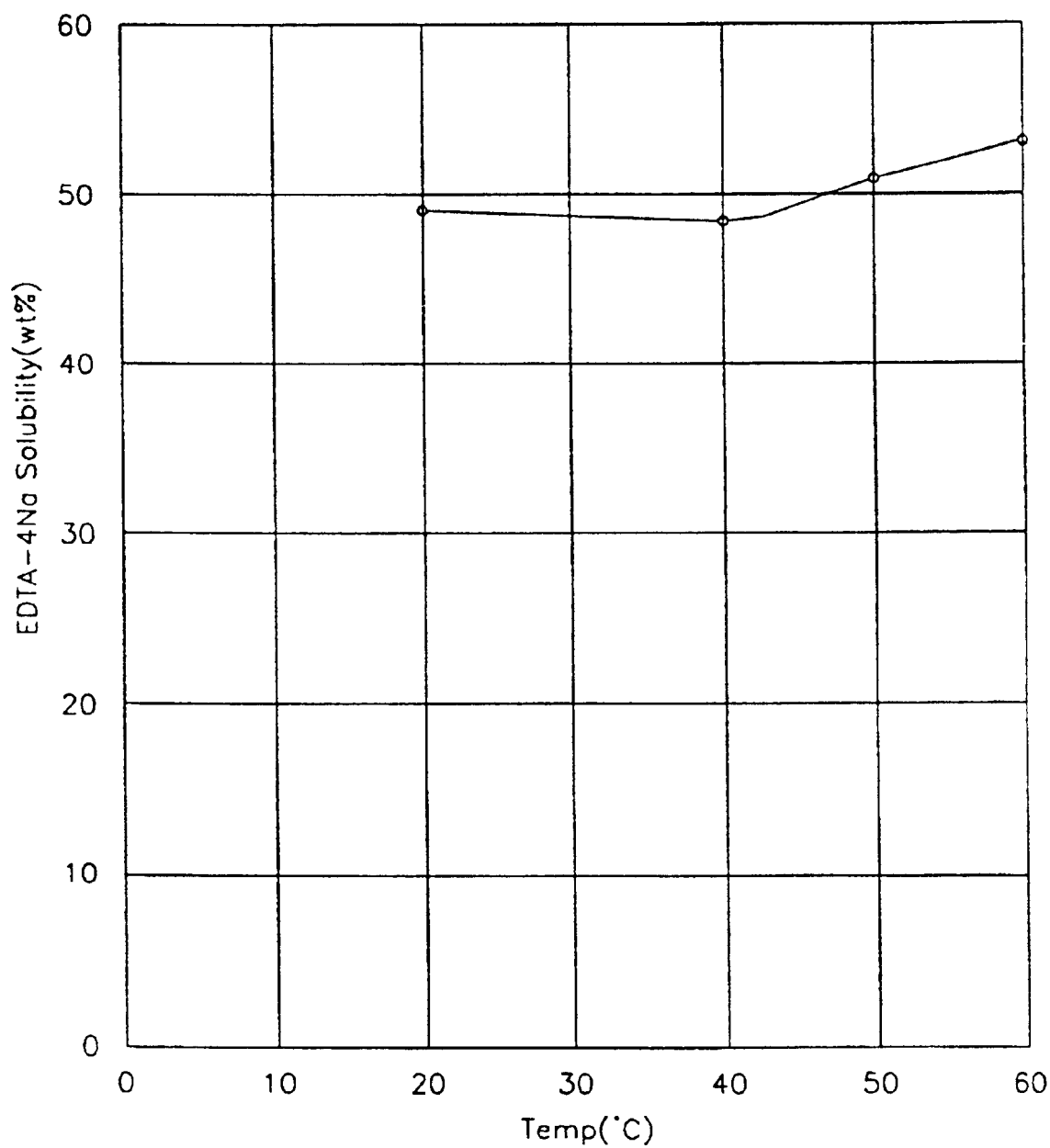
FIG. 1 is a graph depicting the solubility of EDTA-4Na in water depending on the temperature.

The solubility of EDTA-4Na in water was measured by varying the temperature from 20° C. to 60° C. The results are shown in FIG. 1. As can be seen in FIG. 1, the solubility of EDTA-4Na in water is almost constant regardless of temperature. This indicates that crystallization with temperature variation is not effective to obtain EDTA-4Na crystals in water.

Reference Example 2

Figure 2:
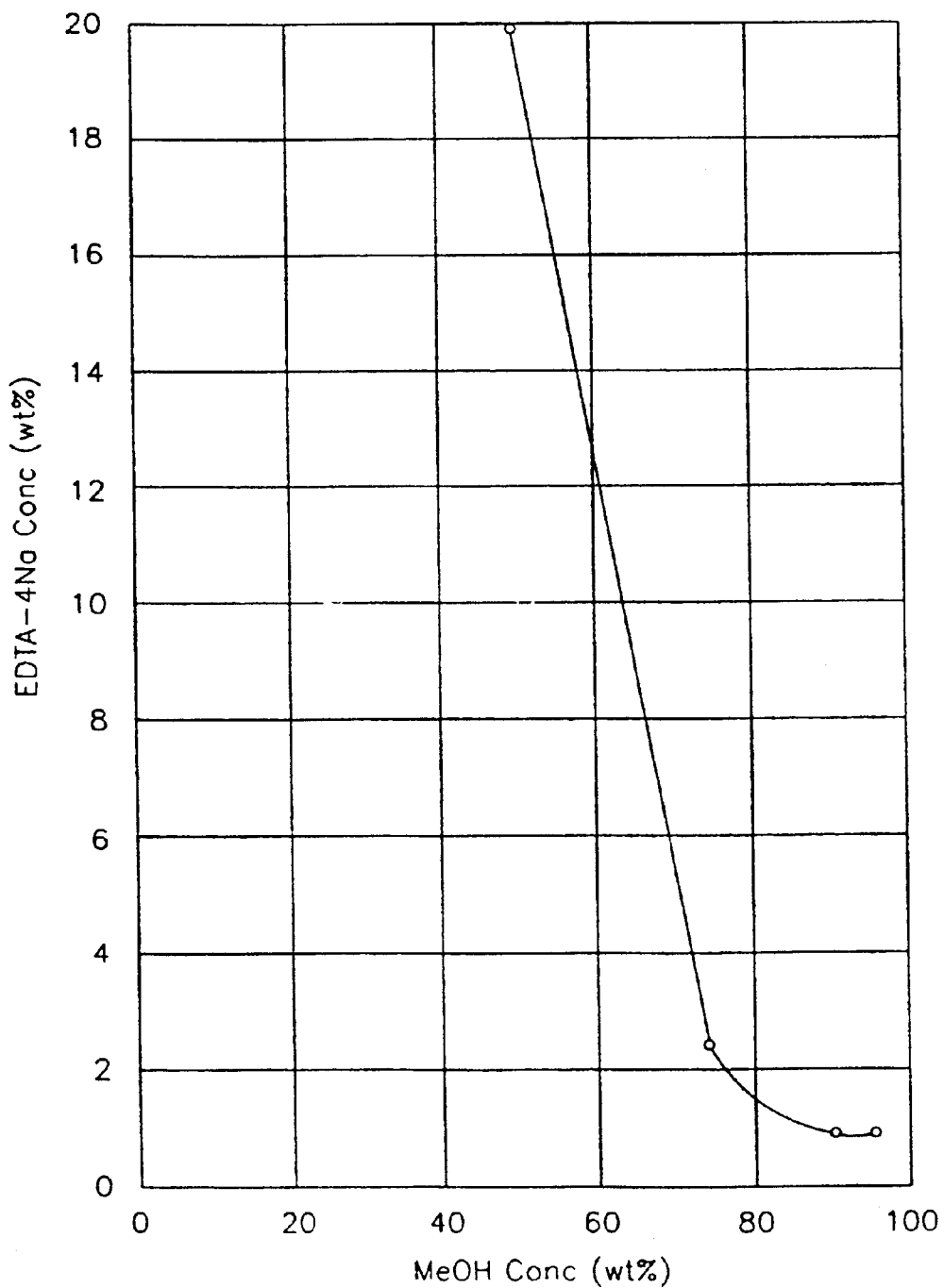
FIG. 2 is a graph depicting the solubility of EDTA-4Na in an aqueous methanol solution depending on the content of menthanol.

The solubility of EDTA-4Na in an aqueous methanol solution was determined by varying the concentration of MeOH in the range of 0 wt % to 100 wt %. The results are shown in FIG. 2. As shown in FIG. 2, the solubility of EDTA-4Na sharply decreases as the methanol concentration increases.

Comparative Example 1

Total Drying Method

The solution (538 g) containing about 40 wt % of EDTA-4Na obtained in Reference Example 1 was dried in a rotary vacuum drier at 80 nmHg, 95° C. The resulting EDTA-4Na was further dried in a thermostat dryer of 110° C. for 3 hours to obtain 253 g of EDTA-4Na (purity 85%).

Comparative Examples 2–9

The solution (200 g) of crude EDTA-4Na (about 40 wt %) obtained in Reference Example 1 was introduced into a 1 liter 5-neck flask equipped with reflux condenser, thermometer and stirrer in a thermostat water bath and the temperature was adjusted to 40–70° C. Methanol in various amounts shown in Table 1 was quantitatively introduced using a quantitative pump and crystallization was carried out for 30–360 minutes shown in Table 1.

The resulting crystal slurry is filtered and dried in a thermostat dryer of 110° C. for 3 hours to yield purified EDTA-4Na. The yield, purity and portion(%) of crystals having a particle diameter less than 30 μm were measured. The results are shown in Table 1. In Table 1, the yield is calculated as following formula:

Yield=Product amount (g)/[Crude EDTA-4Na amount (g)×concentration/100]×100

TABLE 1

| | MeOH (g) | Crystallization Temp (° C.) | MeOh Introduction Time (min) | Yield (wt %) | Purity (wt %) | Portion (%) of < 30 μm |
|---|---|---|---|---|---|---|
| C. Ex. 2 | 200 | 65 | 60 | 55 | 98.5 | 12 |
| C. Ex. 3 | 400 | 65 | 60 | 85 | 98.1 | 22 |
| C. Ex. 4 | 600 | 65 | 120 | 92 | 98.0 | 10 |
| C. Ex. 5 | 400 | 50 | 60 | 65 | 98.0 | 18 |
| C. Ex. 6 | 400 | 40 | 60 | 20 | 98.5 | 25 |
| C. Ex. 7 | 600 | 65 | 360 | 93 | 98.3 | 11 |

TABLE 1-continued

| | MeOH (g) | Crystallization Temp (° C.) | MeOh Introduction Time (min) | Yield (wt %) | Purity (wt %) | Portion (%) of < 30 μm |
|---|---|---|---|---|---|---|
| C. Ex. 8 | 600 | 40 | 360 | 45 | 98.5 | 23 |
| C. Ex. 9 | 400 | 65 | 30 | 83 | 98.1 | 15 |

As can be seen in Table 1, when methanol only is used as a crystallization solvent, the highest yield reaches 93%. Nevertheless, it has a drawback that the final product contains 10 wt % –25 wt % of micro particles having a diameter less than 30 μm, requiring a considerably long filtering time.

Besides, when the same procedure was carried out by using ethanol, propanol or butanol instead of methanol, the resulting crystals of EDTA-4Na were prone to stick to the inner wall of crystallization equipment or a considerably long filtration time was needed as well.

Examples 1–6

The same procedures as Comparative Examples 2–9 were carried out except that mixtures of methanol(MeOH) and ethaol(EtOH) in a weight ratio shown in Table 2 were used instead of methanol only. The results are shown in Table 2.

TABLE 2

| | Ratio of MeOH: EtOH | Ratio of solvent: Crude EDTA-4Na | Crystallization Temp (° C.) | Yield (wt %) | Purity (wt %) | Portion (%) of < 30 μm |
|---|---|---|---|---|---|---|
| Ex. 1 | 1:1 | 2:1 | 65 | 99 | 98.2 | 2 |
| Ex. 2 | 1.4:0.6 | 2:1 | 65 | 95.5 | 98.5 | 5 |
| Ex. 3 | 0.6:1.4 | 2:1 | 65 | 99.5 | 97.9 | 1 |
| Ex. 4 | 1:1 | 2.25:1 | 65 | 100 | 98.5 | 2 |
| Ex. 5 | 1:1 | 2:1 | 50 | 96.5 | 98.0 | 4 |
| Ex. 6 | 1:1 | 2:1 | 40 | 75.3 | 97.9 | 11 |

As can be seen from the results in Table 2, the method of the present invention significantly increases the yield and gives large uniform crystals of EDTA-4Na compared to the conventional method using methanol only.

Thus, for Example 6 and Comparative Example 6, in which the ratio of the crystallization solvent to crude EDTA-4Na was 2:1 and the crystallization temperature was 40° C., the yields of pure EDTA-4Na were 75.3% and 20%, respectively. Moreover, these Examples produced 11% and 25% of particles having a diameter less than 30 μm, respectively.

When comparing Example 5 to Comparative Example 5, in which the ratio of the crystallization solvent to crude EDTA-4Na was 2:1 and the crystallization temperature was 50° C., the yields of pure EDTA-4Na were 96.5% and 65%, respectively. Moreover, these Examples produced 4% and 18% of particles having a diameter less than 3 μm, respectively.

Examples 7–12

The same procedures as Examples 1–6 were carried out except that mixtures of methanol(MeOH) and propanol (PrOH) in a weight ratio shown in Table 3 were used instead of methanol/ethanol mixture. The results are shown in Table 3.

TABLE 3

| | Ratio of MeOH: PrOH | Ratio of solvent: Crude EDTA-4Na | Crystallization Temp (° C.) | Yield (wt %) | Purity (wt %) | Portion (%) of <30 μm |
|---|---|---|---|---|---|---|
| Ex. 7 | 1:1 | 2:1 | 65 | 95.4 | 97.9 | 3 |
| Ex. 8 | 1.4:0.6 | 2:1 | 65 | 99.5 | 98.7 | 4 |
| Ex. 9 | 0.8:1.2 | 2:1 | 65 | 95 | 97.5 | 0.5 |
| Ex. 10 | 1.2:0.8 | 2.25:1 | 65 | 99 | 98.1 | 3.2 |
| Ex. 11 | 1.2:0.8 | 2:1 | 50 | 90 | 98.0 | 4.2 |
| Ex. 12 | 1.2:0.8 | 2:1 | 40 | 97.1 | 97.1 | 5.4 |

Examples 13–16

The same procedures as Examples 1–6 were carried out except that mixtures of methanol(MeOH) and rutanol (BuCH) in a weight ratio shown in Table 4 were used instead of methanol/ethanol mixture. The results are shown in Table 4.

TABLE 4

| | Ratio of MeOH: BuOH | Ratio of solvent Crude EDTA-4Na | Crystallization Temp (° C.) | Yield (wt %) | Purity (wt %) | Portion (%) of <30 μm |
|---|---|---|---|---|---|---|
| Ex. 13 | 1.5:0.5 | 2:1 | 65 | 95.3 | 98.5 | 4.5 |
| Ex. 14 | 1.7:0.3 | 2.25:1 | 65 | 98.8 | 98.5 | 3 |
| Ex. 15 | 1.7:0.3 | 2:1 | 50 | 95.9 | 98.0 | 5 |
| Ex. 16 | 1.7:0.3 | 2:1 | 40 | 55.4 | 97.9 | 10 |

Examples 17–21

Figure 3:
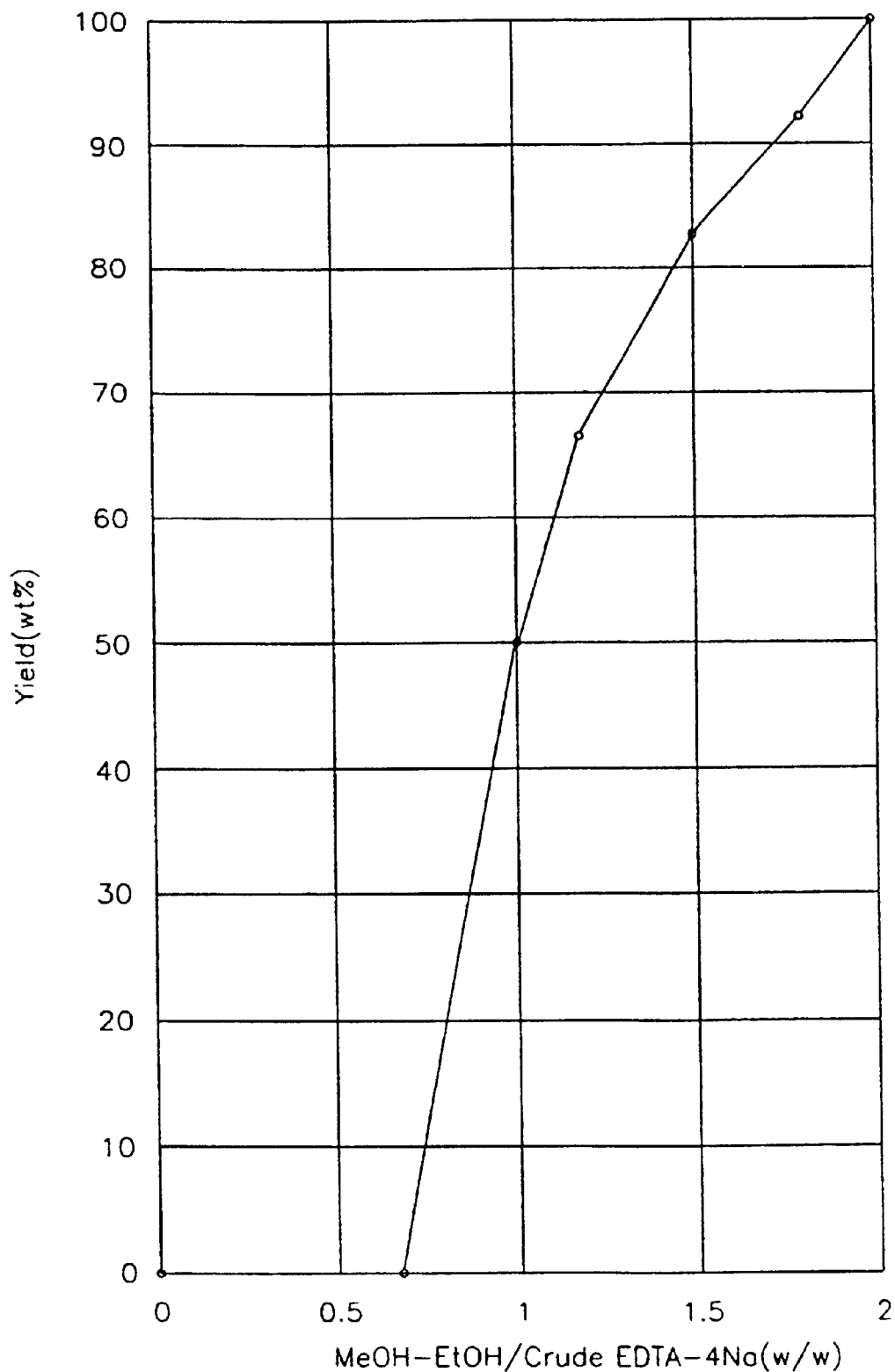
FIG. 3 is a graph depicting the recovery of high purity EDTA-4Na depending on the ratio of methanol:ethanol (1:1) mixture to crude EDTA-4Na.

The same procedures as Examples 1–6 were carried out except that the ratio of the crystallization solvent to crude EDTA-4Na was changed to the range from 0.67:1 to 2:1. The recovery of pure EDTA-4Na was depicted in FIG. 3.

Although preferred embodiments of the present invention have been described in detail herein above, it should be clearly understood that many variations and/or modifications of the basic inventive concepts herein taught which may appear to those skilled in the art will still fall within the spirit and scope of the present invention as defined in the appended claims.

What is claimed is:

1. A method for producing highly purified crystals of tetrasodium, salt of ethylenediaminetetraacetic acid (EDTA4Na), the method comprising:

reacting ethylene diamine, NaCN and formalin in the presence of an alkali to yield a solution containing EDTA4Na and impurities;

subjecting said solution to crystallization over a solvent to form EDTA4Na crystals, said solvent being a mixture of methanol and an alcohol, said alcohol selected from the group consisting of ethanol and propanol, said methanol having a ratio by weight to said alcohol of 1:0.43–4.0; and recovering the EDTA4Na crystals.

2. The method for producing highly purified crystals of EDTA4Na according to claim 1, wherein said solution contains about 40 weight percent of EDTA4Na and wherein a ratio of said solvent to said EDTA4Na in said solution is in the range of 1.25–2.25:1.

3. The method for producing highly purified crystals of EDTA4Na according to claim 1, wherein said step of subjecting said solution to crystallization is carried out at a temperature of about 50° C. to 65° C.

* * * * *